United States Patent
Daon

(10) Patent No.: US 9,452,024 B2
(45) Date of Patent: Sep. 27, 2016

(54) SURGICAL LOCATION MONITORING SYSTEM AND METHOD

(71) Applicant: Navigate Surgical Technologies, Inc., Vancouver (CA)

(72) Inventor: Ehud (Udi) Daon, North Vancouver (CA)

(73) Assignee: Navigate Surgical Technologies, Inc., Vancouver, BC (CA)

( * ) Notice: Subject to any disclaimer, the term of this patent is extended or adjusted under 35 U.S.C. 154(b) by 107 days.

(21) Appl. No.: 14/599,149

(22) Filed: Jan. 16, 2015

(65) Prior Publication Data

US 2015/0132720 A1 May 14, 2015

Related U.S. Application Data

(62) Division of application No. 13/571,284, filed on Aug. 9, 2012, now Pat. No. 8,938,282.

(60) Provisional application No. 61/616,718, filed on Mar. 28, 2012, provisional application No. 61/553,058, filed on Oct. 28, 2011.

(51) Int. Cl.
*A61B 5/05* (2006.01)
*A61B 19/00* (2006.01)
(Continued)

(52) U.S. Cl.
CPC ............... *A61B 19/54* (2013.01); *A61B 1/24* (2013.01); *A61B 5/055* (2013.01); *A61B 5/06* (2013.01);
(Continued)

(58) Field of Classification Search
CPC .......... A61B 10/0233; A61B 17/3211; A61B 19/54; A61B 1/00; A61B 1/24; A61B 2017/00477; A61B 2090/3925; A61B 2090/3954; A61B 2090/3966; A61B 2090/3983; A61B 2090/3991; A61B 34/20; A61B 5/055; A61B 5/06; A61B 5/062; A61B 5/064; A61B 5/72; A61B 6/032; A61B 6/12; A61B 6/14; A61B 6/145; A61B 6/52; A61B 8/0841; A61B 90/16; A61B 90/39; A61C 19/04; A61C 1/0007; A61C 1/082; A61C 3/02
See application file for complete search history.

(56) References Cited

U.S. PATENT DOCUMENTS 5,230,623 A 7/1993 Guthrie
5,438,991 A 8/1995 Yu et al.
(Continued)

FOREIGN PATENT DOCUMENTS

DE 2005026654 12/2006
DE 2009009158 9/2010
(Continued)

OTHER PUBLICATIONS

European Patent Office, Written Opinion of the International Searching Authority, International Application No. PCT/IL2015/050400, Navigate Surgical Technologies, Inc., Jul. 16, 2015.
(Continued)

*Primary Examiner* — Mark Remaly
(74) *Attorney, Agent, or Firm* — Kevin R. Erdman; Brannon Sowers & Cracraft PC

(57) ABSTRACT

The present invention involves a surgical hardware and software monitoring system and method which allows for surgical planning while the patient is available for surgery, for example while the patient is being prepared for surgery so that the system may model the surgical site. In one embodiment, the model may be used to track contemplated surgical procedures and warn the physician regarding possible boundary violations that would indicate an inappropriate location in a surgical procedure. In another embodiment, the hardware may track the movement of instruments during the procedure and in reference to the model to enhance observation of the procedure.

20 Claims, 11 Drawing Sheets

(51) Int. Cl.
| | |
|---|---|
| *A61B 5/06* | (2006.01) |
| *A61B 5/00* | (2006.01) |
| *A61B 5/055* | (2006.01) |
| *A61B 6/12* | (2006.01) |
| *A61B 6/00* | (2006.01) |
| *A61B 1/24* | (2006.01) |
| *A61C 3/02* | (2006.01) |
| *A61B 17/3211* | (2006.01) |
| *A61B 6/03* | (2006.01) |
| *A61B 6/14* | (2006.01) |
| *A61C 1/08* | (2006.01) |
| *A61B 8/08* | (2006.01) |
| *A61C 19/04* | (2006.01) |
| *A61B 1/00* | (2006.01) |
| *A61B 10/02* | (2006.01) |
| *A61C 1/00* | (2006.01) |
| *A61B 17/00* | (2006.01) |

(52) U.S. Cl.
CPC .............. *A61B 5/062* (2013.01); *A61B 5/064* (2013.01); *A61B 5/72* (2013.01); *A61B 6/032* (2013.01); *A61B 6/12* (2013.01); *A61B 6/145* (2013.01); *A61B 6/52* (2013.01); *A61B 8/0841* (2013.01); *A61B 17/3211* (2013.01); *A61B 34/20* (2016.02); *A61B 90/16* (2016.02); *A61B 90/39* (2016.02); *A61C 1/082* (2013.01); *A61C 3/02* (2013.01); *A61C 19/04* (2013.01); *A61B 1/00* (2013.01); *A61B 6/14* (2013.01); *A61B 10/0233* (2013.01); *A61B 2017/00477* (2013.01); *A61B 2090/3925* (2016.02); *A61B 2090/3954* (2016.02); *A61B 2090/3966* (2016.02); *A61B 2090/3983* (2016.02); *A61B 2090/3991* (2016.02); *A61C 1/0007* (2013.01)

(56) References Cited

U.S. PATENT DOCUMENTS

| | | | |
|---|---|---|---|
| 5,603,318 | A | 2/1997 | Heilbrun et al. |
| 5,828,770 | A | 10/1998 | Leis et al. |
| 5,967,777 | A | 10/1999 | Klein |
| 6,122,541 | A | 9/2000 | Cosman et al. |
| 6,468,265 | B1 | 10/2002 | Evans et al. |
| 6,529,765 | B1 | 3/2003 | Franck et al. |
| 7,653,455 | B2 | 1/2010 | Cinador |
| 7,720,521 | B2 | 5/2010 | Chang |
| 7,758,345 | B1 | 7/2010 | Christensen |
| 7,894,878 | B2 | 2/2011 | Noujeim |
| 7,899,512 | B2 | 3/2011 | Labadie |
| 8,172,573 | B2 | 5/2012 | Sonenfeld |
| 2004/0002642 | A1 | 1/2004 | Dekel et al. |
| 2004/0097952 | A1 | 5/2004 | Sarin et al. |
| 2004/0138556 | A1 | 7/2004 | Cowman |
| 2005/0085719 | A1 | 4/2005 | Franklin et al. |
| 2005/0163342 | A1 | 7/2005 | Persky |
| 2005/0182318 | A1 | 8/2005 | Kaji et al. |
| 2006/0142657 | A1 | 6/2006 | Quaid et al. |
| 2006/0165310 | A1 | 7/2006 | Mack |
| 2006/0212044 | A1 | 9/2006 | Bova et al. |
| 2006/0247517 | A1 | 11/2006 | Labadie et al. |
| 2006/0281991 | A1 | 12/2006 | Fitzpatrick |
| 2007/0208252 | A1 | 9/2007 | Makower |
| 2007/0223910 | A1 | 9/2007 | Aoki |
| 2007/0253541 | A1 | 11/2007 | Sukovic et al. |
| 2008/0026338 | A1 | 1/2008 | Cinader |
| 2008/0161682 | A1 | 7/2008 | Kendrick et al. |
| 2008/0171305 | A1 | 7/2008 | Sonenfeld et al. |
| 2008/0183071 | A1 | 7/2008 | Strommer |
| 2008/0193896 | A1 | 8/2008 | Yang |
| 2008/0200927 | A1 | 8/2008 | Hartmann et al. |
| 2008/0262345 | A1 | 10/2008 | Fichtinger |
| 2008/0319491 | A1 | 12/2008 | Schoenefeld |
| 2009/0012509 | A1 | 1/2009 | Csavoy |
| 2009/0171196 | A1 | 7/2009 | Olson et al. |
| 2009/0253095 | A1 | 10/2009 | Salcedo |
| 2010/0039506 | A1 | 2/2010 | Sarvestani et al. |
| 2010/0049195 | A1 | 2/2010 | Park et al. |
| 2010/0168562 | A1 | 7/2010 | Zhao et al. |
| 2010/0168763 | A1 | 7/2010 | Zhao et al. |
| 2010/0210939 | A1 | 8/2010 | Hartmann et al. |
| 2010/0217139 | A1 | 8/2010 | Pinter et al. |
| 2011/0008751 | A1 | 1/2011 | Patterssen |
| 2011/0087332 | A1 | 4/2011 | Bojarski et al. |
| 2011/0217667 | A1 | 9/2011 | Groscruth |
| 2011/0257653 | A1 | 10/2011 | Hughes |
| 2012/0065496 | A1 | 3/2012 | Stratton |
| 2012/0115107 | A1 | 5/2012 | Adams |
| 2012/0259204 | A1 | 10/2012 | Carrat et al. |
| 2012/0283637 | A1 | 11/2012 | Cohen |
| 2013/0063558 | A1 | 3/2013 | Phipps |
| 2013/0258353 | A1 | 10/2013 | Kosmecki et al. |
| 2013/0332271 | A1 | 12/2013 | Doron et al |
| 2014/0030669 | A1 | 1/2014 | Hey et al. |
| 2014/0049629 | A1 | 2/2014 | Siewerdsen et al. |

FOREIGN PATENT DOCUMENTS

| | | |
|---|---|---|
| DE | 2010042540 | 4/2012 |
| DE | 2011012460.8 | 8/2012 |
| EP | 1527417 | 9/2011 |
| FR | 2 929 794 | 10/2009 |
| GB | 2 416 949 | 2/2006 |
| JP | 2000046546 | 2/2000 |
| JP | 2007253748 | 10/2007 |
| JP | 2009172411 | 5/2009 |
| WO | 99/27839 | 6/1999 |
| WO | 02/076302 | 10/2002 |
| WO | 2008/009136 | 1/2008 |
| WO | 2010/086374 | 5/2010 |
| WO | 2011/109041 | 9/2011 |
| WO | 2011113441 | 9/2011 |
| WO | 2012068679 | 5/2012 |
| WO | 2012095642 | 7/2012 |
| WO | 2012149548 | 11/2012 |
| WO | 2013096766 | 6/2013 |
| WO | 2013144208 | 10/2013 |
| WO | 2013144939 | 10/2013 |

OTHER PUBLICATIONS

European Patent Office, International Search Report, International Application No. PCT/IL2015/050400, Navigate Surgical Technologies, Inc., Jul. 16, 2015.
USPTO, Non-Final Office Action for U.S. Appl. No. 13/744,967, dated Jun. 30, 2015.
USPTO, Non-Final Office Action for U.S. Appl. No. 13/745,249, dated Jun. 30, 2015.
USPTO, Final Office Action for U.S. Appl. No. 13/745,763, dated Jul. 8, 2015.
Arizona Center for Laser Dentistry, Root Canals at the Arizona Center for Laser Dentistry, Captured via web.archive.org on Dec. 19, 2010, retrieved Jun. 2, 2015.
European Patent Office, International Written Opinion, dated Sep. 29, 2014 (PCT/IB2014/060403).
European Patent Office, International Written Opinion, dated Oct. 17, 2014 (PCT/EP2014/067280).
European Patent Office, International Search Report, dated Jul. 17, 2014 (PCT/EP2014/058406).
European Patent Office, International Written Opinion, dated Aug. 18, 2014 (PCT/EP2014/058406).
European Patent Office, International Written Opinion, dated Jul. 30, 2014 (PCT/EP2014/057656).
European Patent Office, International Written Opinion, dated Jul. 30, 2014 (PCT/EP2014/060018).
EPO, International Search Report and Written Opinion for PCT/EP/2013/073401, Mar. 7, 2014.
European Patent Office, International Search Report, dated Sep. 3, 2013 (PCT/IL2013/000032).

(56) References Cited

OTHER PUBLICATIONS

European Patent Office, International Written Opinion, dated Sep. 3, 2013 (PCT/IL2013/000032).
European Patent Office, International Search Report, dated Sep. 16, 2013 (PCT/EP2013/056525).
European Patent Office, International Written Opinion, dated Sep. 16, 2013 (PCT/EP2013/056525).
European Patent Office, International Search Report, mailed Sep. 17, 2013 (PCT/IL2013/000031).
European Patent Office, International Written Opinion, mailed Sep. 17, 2013 (PCT/IL2013/000031).
Prosecution of U.S. Appl. No. 13/571,284, from First Office Action of Aug. 15, 2013 to Amendment with Request for Continued Examination of Feb. 26, 2014.
European Patent Office, International Search Report, mailed Mar. 4, 2013 (PCT/IL2012/000363).
European Patent Office, International Written Opinion, mailed Mar. 4, 2013 (PCT/IL2012/000363).
European Patent Office, International Search Report, dated Feb. 18, 2014 (PCT/EP2013/073416).
European Patent Office, International Written Opinion, dated Feb. 18, 2014 (PCT/EP2013/073416).
European Patent Office, International Search Report, International Application No. PCT/EP2013/073401, dated Mar. 19, 2014.
European Patent Office, Written Opinion of the International Searching Authority, International Application No. PCT/EP2013/073401, dated Mar. 19, 2014.
European Patent Office, International Search Report, International Application No. PCT/EP2014/057656, dated Aug. 11, 2014.
European Patent Office, Written Opinion of the International Searching Authority, International Application No. PCT/EP2014/051656, dated Aug. 11, 2014.
European Patent Office, International Search Report, International Application No. PCT/EP2014/060018, dated Aug. 11, 2014.
European Patent Office, Written Opinion of the International Searching Authority, International Application No. PCT/EP2014/060018, dated Aug. 11, 2014.
European Patent Office, Written Opinion of the International Searching Authority, International Application No. PCT/EP2014/067279, dated Nov. 7, 2014.
European Patent Office, Written Opinion of the International Searching Authority, International Application No. PCT/EP2014/067280, dated Oct. 27, 2014.
USPTO, Non-Final Office Action for U.S. Appl. No. 13/571,284, dated Aug. 15, 2013.
USPTO, Non-Final Office Action for U.S. Appl. No. 13/713,165, dated Aug. 13, 2014.
Japanese Patent Office (JPO) Notice of Preliminary Rejection,Japan Patent Application No. 2014-537811, Based upon PCT/IL2012/000363, Jan. 25, 2016, which claims priority to U.S. Appl. No. 13/571,284, now U.S. Pat. No. 8,938,282.
Japanese Patent Office (JPO) Notice of Preliminary Rejection,Japanese Patent Application No. 2015-541159, Based upon PCT/EP2013/0073401, Mar. 1, 2016, which claims priority to U.S. Appl. No. 14/562691, now U.S. Pat. No. 8,908,918.
USPTO, Non-Final Office Action for U.S. Appl. No. 13/822,358, dated Feb. 13, 2015.
USPTO, Response to Non-Final Office Action for U.S. Appl. No. 13/745,765, dated Mar. 25, 2015.

SURGICAL LOCATION MONITORING SYSTEM AND METHOD

CROSS REFERENCE TO RELATED APPLICATIONS

The present application is a divisional of U.S. application Ser. No. 13/571,284, filed on Aug. 9, 2012, which claims priority from U.S. Provisional Patent Application Ser. Nos. 61/553,058 and 61/616,718 filed on Oct. 28, 2011, and Mar. 28, 2012 respectively, said Non-Provisional and Provisional applications all entitled the same as the present application, the disclosures of which are expressly incorporated by reference herein.

BACKGROUND OF THE INVENTION

1. Field of the Invention

The invention relates to location monitoring hardware and software systems. More specifically, the field of the invention is that of surgical equipment and software for monitoring surgical conditions.

2. Description of the Related Art

Visual and other sensory systems are known, with such systems being capable of both observing and monitoring surgical procedures. With such observation and monitoring systems, computer aided surgeries are now possible, and in fact are being routinely performed. In such procedures, the computer software interacts with both clinical images of the patient and observed surgical images from the current surgical procedure to provide guidance to the physician in conducting the surgery. For example, in one known system a carrier assembly bears at least one fiducial marker onto an attachment element in a precisely repeatable position with respect to a patient's jaw bone, employing the carrier assembly for providing registration between the fiducial marker and the patient's jaw bone and implanting the tooth implant by employing a tracking system which uses the registration to guide a drilling assembly. With this relatively new computer implemented technology, further improvements may further advance the effectiveness of surgical procedures.

SUMMARY OF THE INVENTION

The present invention is a surgical hardware and software monitoring system and method which allows for surgical planning while the patient is available for surgery, for example while the patient is being prepared for surgery so that the system may model the surgical site. In one embodiment, the model may be used to track contemplated surgical procedures and warn the physician regarding possible boundary violations that would indicate an inappropriate location in a surgical procedure. In another embodiment, the hardware may track the movement of instruments during the procedure and in reference to the model to enhance observation of the procedure. In this way, physicians are provided an additional tool to improve surgical planning and performance.

The system uses a particularly configured piece of hardware, termed a key, to orient the monitoring system with regard to the critical area. The key is attached to a location near the intended surgical area. For example, in the example of a dental surgery, a splint may be used to securely locate the key near the surgical area. The key may then be used as a point of reference, or a fiducial, for the further image processing of the surgical site. The key may be identified relative to other portions of the surgical area by having a recognizable fiducial marker apparent in the scan.

Using the dental surgery example, the patient is scanned, for example by an x-ray, magnetic resonance imaging (MRI), computerized tomography (CT), or cone beam computerized tomography (CBCT), to obtain an initial image of the surgical site. The particular configuration of the key allows computer software to recognize its relative position within the surgical site, so that further observations may be made with reference to both the location and orientation of the key. In fact, the computer software may create a coordinate system for organizing objects in the scan, such as teeth, jaw bone, skin and gum tissue, other surgical instruments, etc.

In one embodiment, the computer system has a predetermined knowledge of the configuration of the key and examines slices of the scan to locate the material density of the key. Once the fiducial is located and the key is segmented so that a point, which may or may not be within the key, is arbitrarily assigned as the center of the coordinate system. Then a transformation matrix from the known actual fiducial pattern and the analyzed image is created to realize the coordinate system encompassing the surgical site. The resulting virtual construct may then be used by surgical procedure planning software for virtual modeling of the contemplated procedure, and may alternatively be used by instrumentation software for the configuration of the instrument, for providing imaging assist for surgical software, and/or for plotting trajectories for the conduct of the surgical procedure In one embodiment, the monitoring hardware includes a trackable pole that is attachable to the key and which has a particular identifying pattern. The attachment and the pole itself have known configurations so that observational data from the pole may be precisely mapped to the coordinate system and thus the progress of the surgical procedure may be monitored and recorded. For example, the key may have a hole in a predetermined location specially adapted for engagement with the pole. In such an arrangement, for example, the poles may be attached with a low force push into the hole of the key, and an audible haptic notification may thus be given upon successful completion of the attachment.

It is further possible to reorient the pole during a surgical procedure. Such reorientation may be to change the location of the procedure, for example where a dental surgery deals with teeth on the opposite side of the mouth, where a surgeon switches hands, and/or where a second surgeon performs a portion of the procedure. For example, the movement of the pole may trigger a re-registration of the pole with relation to the coordinate system, so that the locations may be accordingly adjusted. Additionally, boundary conditions may be implemented in the software so that the user is notified when observational data approaches and/or enters the boundary areas. Further items in the surgical area may also have markers, and be identified during procedures by the markers.

In a further embodiment of the system utilizing the invention, a surgical instrument, termed a "hand piece," may also have a particular configuration that may be located and tracked in the coordinate system. A boundary condition may be set up to indicate a potential collision with virtual material, so that when the hand piece is sensed to approach the boundary condition an indication may appear on a screen, or an alarm sound. Further, target boundary conditions may be set up to indicate the desired surgical area, so that when the trajectory of the hand piece is trending outside the target area an indication may appear on screen or an alarm sound indicating that the hand piece is deviating from its desired path. Other items in the surgical area may also have recognizable codes so that their position and orientation may be determined simply by recognition of the code.

The system of embodiments of the invention involves automatically computing patient location compared with the pole as a tracking device. In the dental surgery example, the key has a pole that is mechanically connected to its base key that is fixated in patient mouth. Each pole tracking device has a particular observation pattern, and a particular geometrical connection to base, which the computer software recognizes corresponds to a particular geometry for subsequent location calculations. Although individual pole tracking devices have distinct configurations, they all share the same connection base and thus may be used with any key. The particular tracking information calculations are dictated by the particular pole tracker used, and actual patient location is calculated accordingly. Thus, pole tracking devices may be interchanged and calculation of the location remains the same. This provides, in the case of dental surgery, automatic recognition of the patient head location in space. Alternatively, the pole may have a sensor device, or a tracker, in a known position relative to the fiducial reference so that the current data image may be mapped to the scan image items.

The key and each pole or marker may have a pattern made of radio opaque material so that when imaging information is scanned by the software, the particular items are recognized. Typically, each instrument used in the procedure has a unique pattern on its associated marker so that the tracker information identifies the instrument. The software creates a model of the surgical site, in one embodiment a coordinate system, according to the location and orientation of the patterns on the key and/or pole(s). In the embodiment where the key has a pre-assigned pattern, the tracker analyzing software recognizes the site of base and selects the fiducial, for example at the location where the key is attached to a splint. If the key does not contain a pattern, a fiducial site is designated, in the dental example at a particular relation to the tooth, and a splint location is automatically designed for placement of the key.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
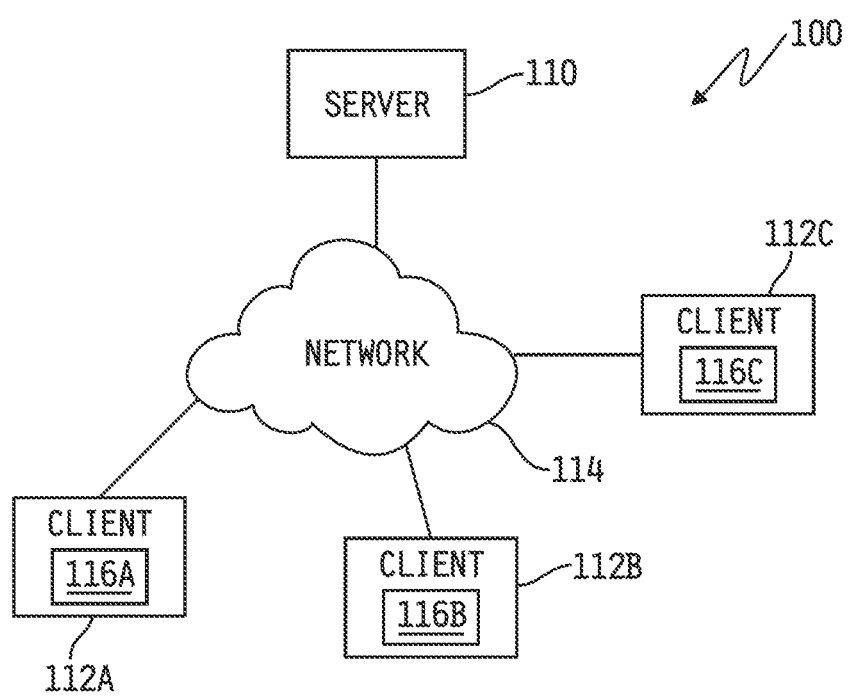
FIG. 1 is a schematic diagrammatic view of a network system in which embodiments of the present invention may be utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

The detailed descriptions which follow are presented in part in terms of algorithms and symbolic representations of operations on data bits within a computer memory representing alphanumeric characters or other information. The hardware components are shown with particular shapes and relative orientations and sizes using particular scanning techniques, although in the general case one of ordinary skill recognizes that a variety of particular shapes and orientations and scanning methodologies may be used within the teaching of the present invention. A computer generally includes a processor for executing instructions and memory for storing instructions and data, including interfaces to obtain and process imaging data. When a general purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities, observing and measuring scanned data representative of matter around the surgical site. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed to capture the underlying data of an image. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements which impart or manifest a physical organization on the information stored in memory. More than mere abstraction, the data structures are specific electrical or magnetic structural elements in memory which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the present invention; the operations are machine operations. Useful machines for performing the operations of the present invention include general purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

The present invention also relates to an apparatus for performing these operations. This apparatus may be specifically constructed for the required purposes or it may comprise a general purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipments through signals configured to particular protocols which may or may not require specific hardware or programming to interact. In particular, various general purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects. Often, but not necessarily, a physical object has a corresponding software object, that may collect and transmit observed data from the physical device to the software system. Such observed data may be accessed from the physical object and/or the software object merely as an item of convenience, therefore where "actual data" is used in the following description, such "actual data" may be from the instrument itself or from the corresponding software object or module.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system can be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms which are used frequently have specialized meanings in the present context. The term "object" relates to a set of computer instructions and associated data which can be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks can access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a world wide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information which is formatted in a Standard Generalized Markup Language ("SGML") or a HyperText Markup Language ("HTML"), both being scripting languages which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"). Fourth Generation (broadband or "4G"), personal digital cellular ("PDC"), or through packet-data technology over analog systems such as cellular digital packet data ("CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7. "Mobile Apps" refers to software programs written for execution with Mobile Software.

The terms "scan," "fiducial reference," "marker," and "tracker" have particular meanings in the present disclosure. For purposes of the present disclosure, "scan" or derivatives thereof refer to x-ray, magnetic resonance imaging (MRI), computerized tomography (CT), sonography, cone beam computerized tomography (CBCT), or any system which produces a quantitative spatial representation of a patient. The term "fiducial reference" or simply "fiducial" refers to an object or reference on the image of a scan that is uniquely identifiable as a fixed recognizable point. The term "marker" refers to an object or reference that may be perceived by a sensor proximate to the location of the surgical or dental procedure, where the sensor may be an optical sensor, a radio frequency identifier (RFID), a sonic motion detector, an ultra-violet or infrared sensor. The term "tracker" refers to a device or system of devices able to determine the location of the markers and their orientation and movement continually in 'real time' during a procedure. As an example of a possible implementation, if the markers are composed of printed targets then the tracker may include a stereo camera pair. As another example of a possible implementation, if the tracker pole has a fixed and known orientation relative to the fiducial, then the tracker may simply be a marker that serves to orient and position the other instruments having markers that are apparent to a separate sensor.

FIG. 1 is a high-level block diagram of a computing environment 100 according to one embodiment. FIG. 1 illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 2:
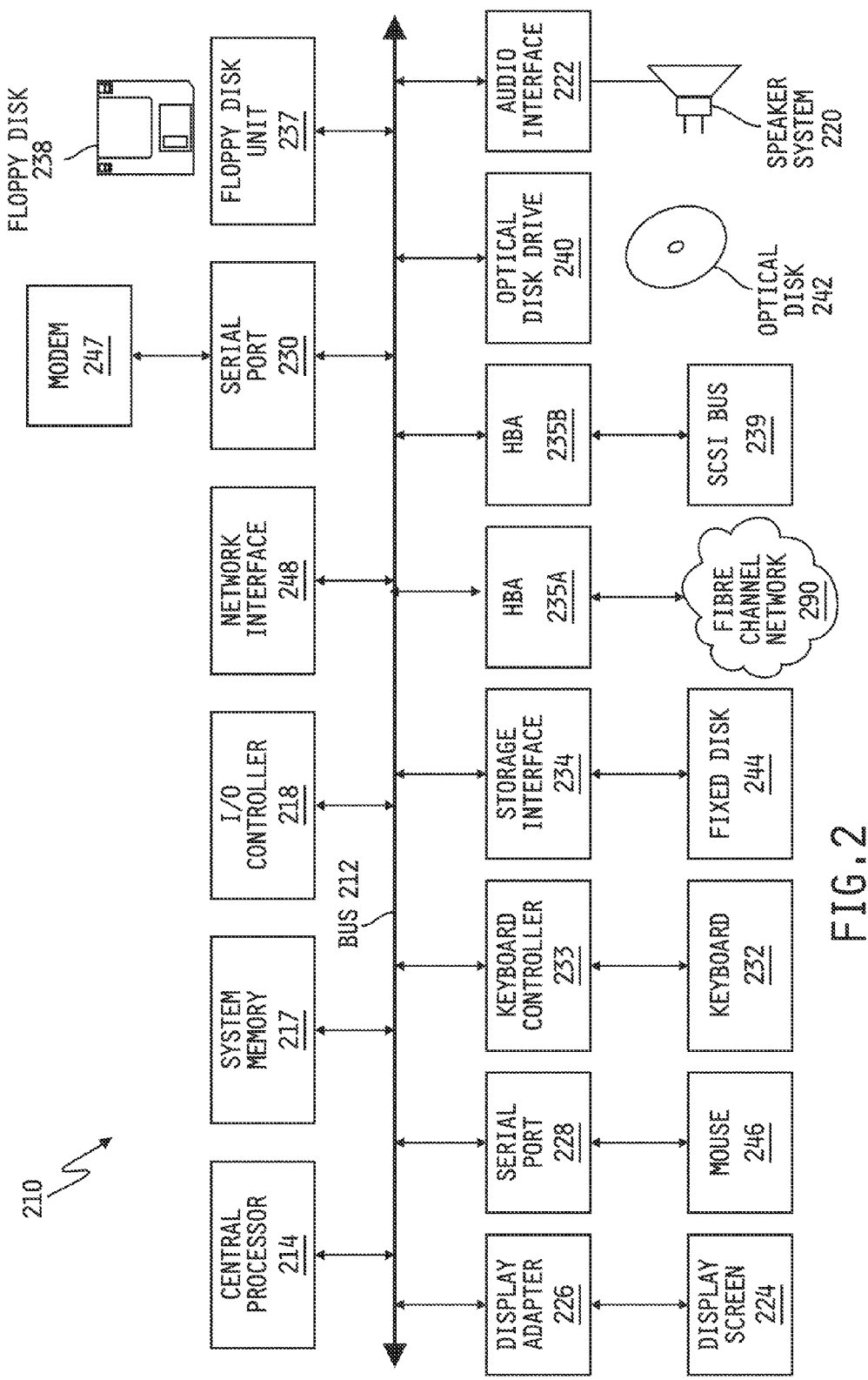
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238, host bus adapter (HBA) interface card 235A operative to connect with Fibre Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS) which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on), including the hardware components of FIGS. 3A-I, which alternatively may be in communication with associated computational resources through local, wide-area, or wireless networks or communications systems. Thus, while the disclosure may generally discuss an embodiment where the hardware components are directly connected to computing resources, one of ordinary skill in this area recognizes that such hardware may be remotely connected with computing resources. Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

The present invention relates to a surgical hardware and software monitoring system and method which allows for surgical planning while the patient is available for surgery, for example while the patient is being prepared for surgery so that the system may model the surgical site. The system uses a particularly configured piece of hardware, represented as key 10 in FIG. 3A, to orient tracking marker 12 of the monitoring system with regard to the critical area of the surgery. Key 10 is attached to a location near the intended surgical area, in the exemplary embodiment of the dental surgical area of FIG. 3A where key 10 is attached to splint 14. Tracking marker 12 is connected to key 10 by pole 11. For example, in the example of a dental surgery, splint 14 may be used to securely locate key 10 near the surgical area. Key 10 may then be used as a point of reference, or a fiducial, for the further image processing of the surgical site from data acquired by tracking marker 12. In alternative embodiments, not shown, tracking marker 12 may be independent of pole 11 in which case pole 11 has a tracker to sense and orient the position of tracking marker 12 relative to the scan data of the surgical area.

Using the dental surgery example, the patient is scanned to obtain an initial scan of the surgical site. The particular configuration of the key allows computer software to recognize its relative position within the surgical site, so that further observations may be made with reference to both the location and orientation of the key. In some embodiments, the fiducial reference includes a marking that is apparent when scanned as a recognizable symbol. In other embodiments, the fiducial reference includes a shape that is distinct in the sense that the body apparent on the scan has an asymmetrical form allowing the front, rear, upper, and lower, and left/right defined surfaces that may be unambiguously determined from the analysis of the scan.

In addition, the computer software may create a coordinate system for organizing objects in the scan, such as teeth, jaw bone, skin and gum tissue, other surgical instruments, etc. The coordinate system relates the images on the scan to the space around the fiducial and locates the instruments with markers both by orientation and position. The model may then be used to check boundary conditions, and in conjunction with the tracker display the arrangement in real time.

In one embodiment, the computer system has a predetermined knowledge of the configuration of the key and examines slices of the scan to locate the material density of the key. Once the fiducial is located and the key is segmented so that a point within the key is arbitrarily assigned as the center of the coordinate system. Then a model in the form of a transformation matrix from the known actual key or fiducial pattern and the analyzed image is created to realize the coordinate system encompassing the surgical site. The resulting virtual construct may then be used by surgical procedure planning software for virtual modeling of the contemplated procedure, and may alternatively be used by instrumentation software for the configuration of the instrument, for providing imaging assist for surgical software, and/or for plotting trajectories for the conduct of the surgical procedure.

Figure 3A:
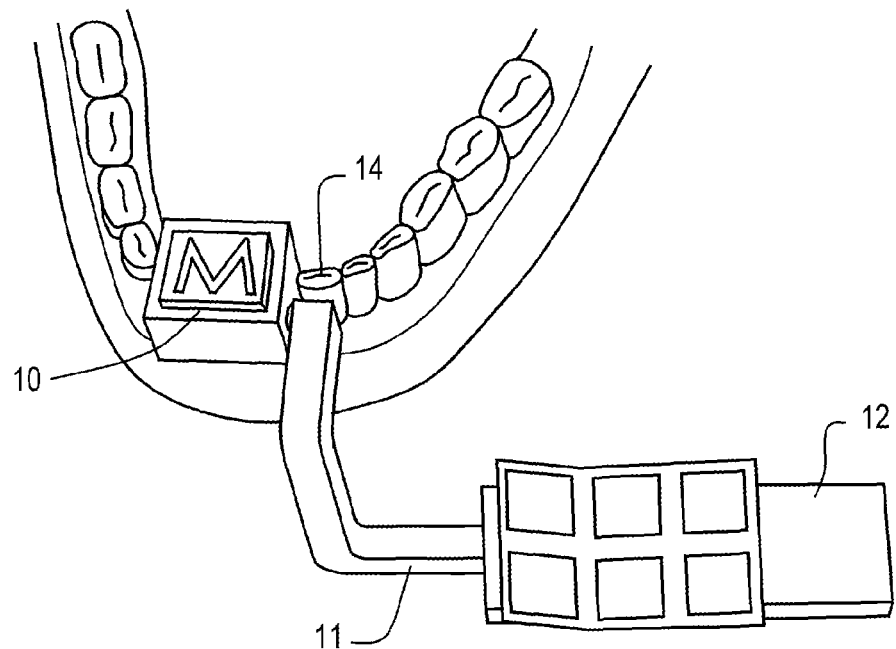
FIGS. 3A-J are drawings of hardware components of the monitoring system according to embodiments of the invention.
Figure 3B:
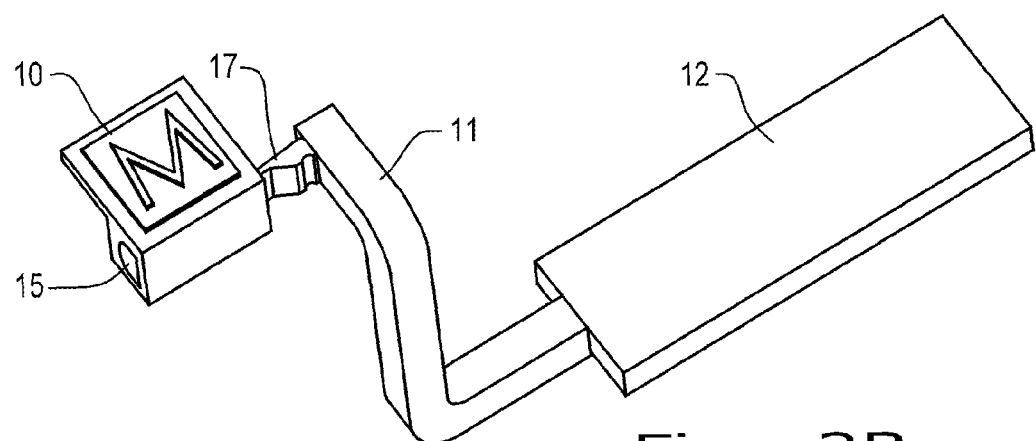
Figure 3C:
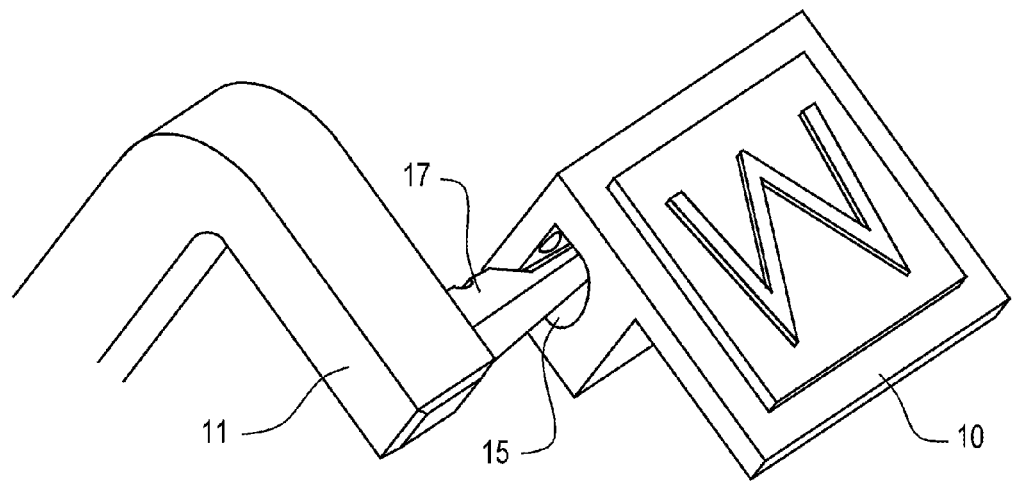
Figure 3D:
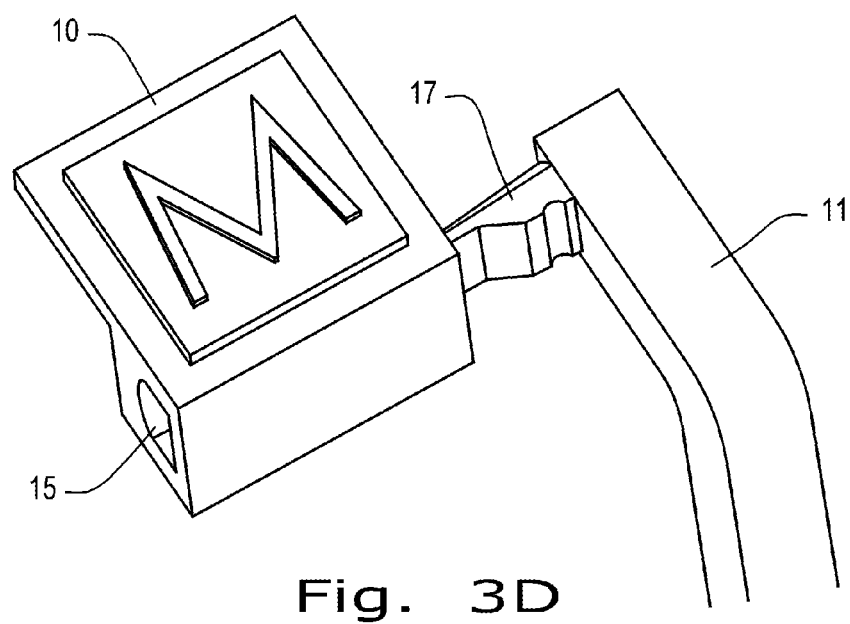
Figure 3E:
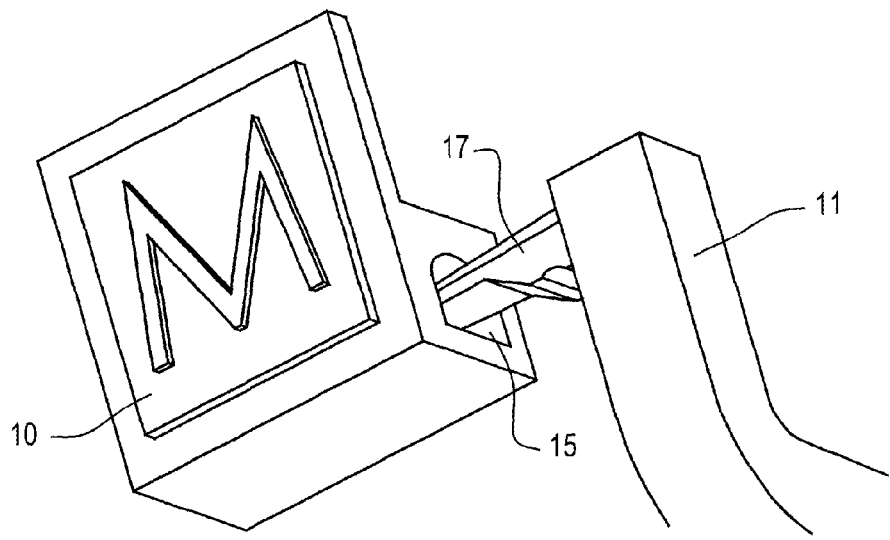
Figure 3F:
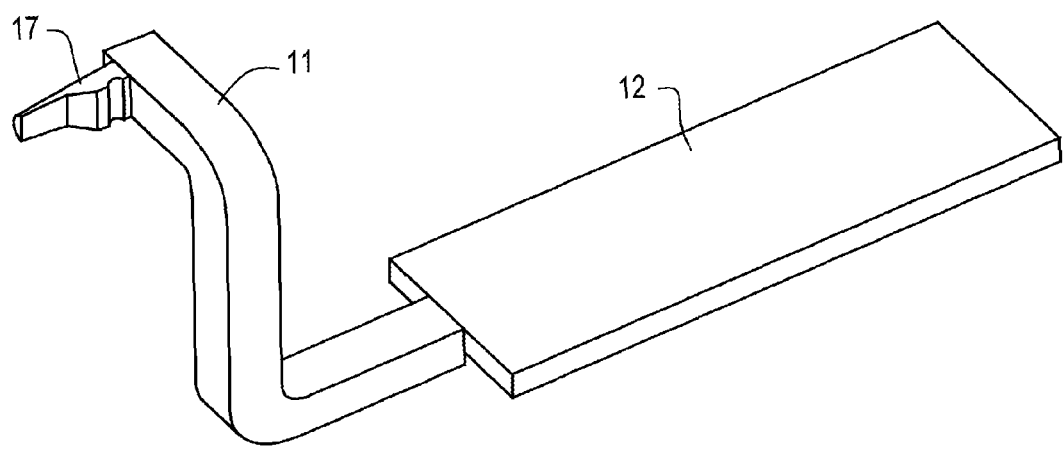
Figure 3G:
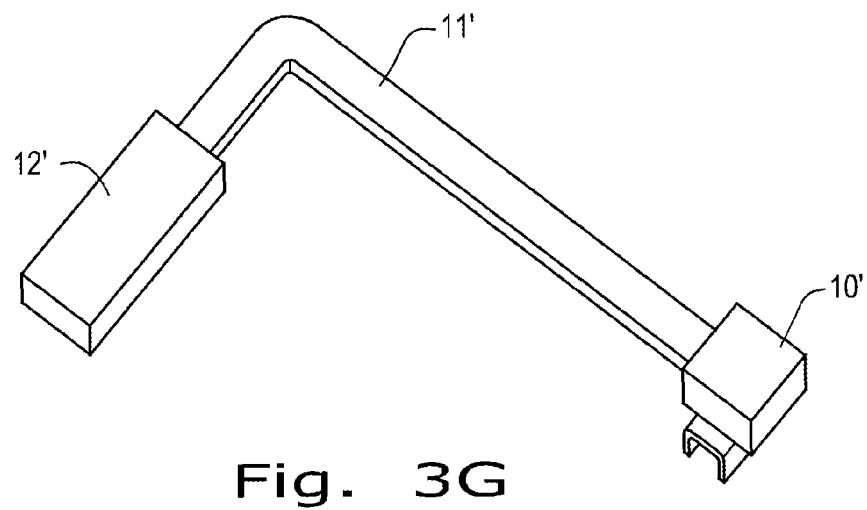
Figure 3H:
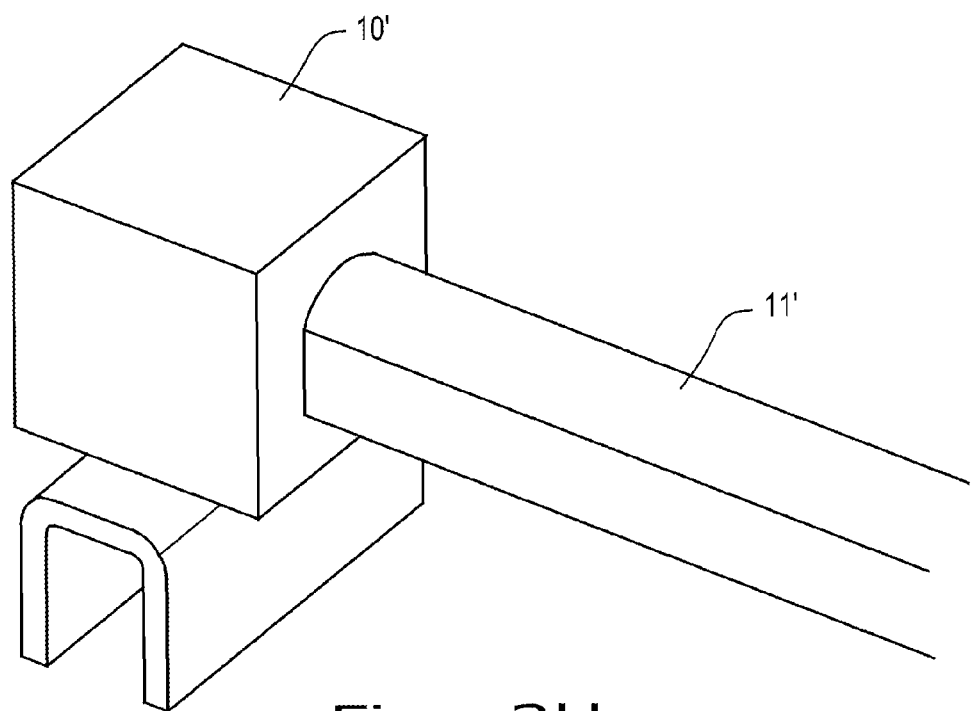
Figure 3I:
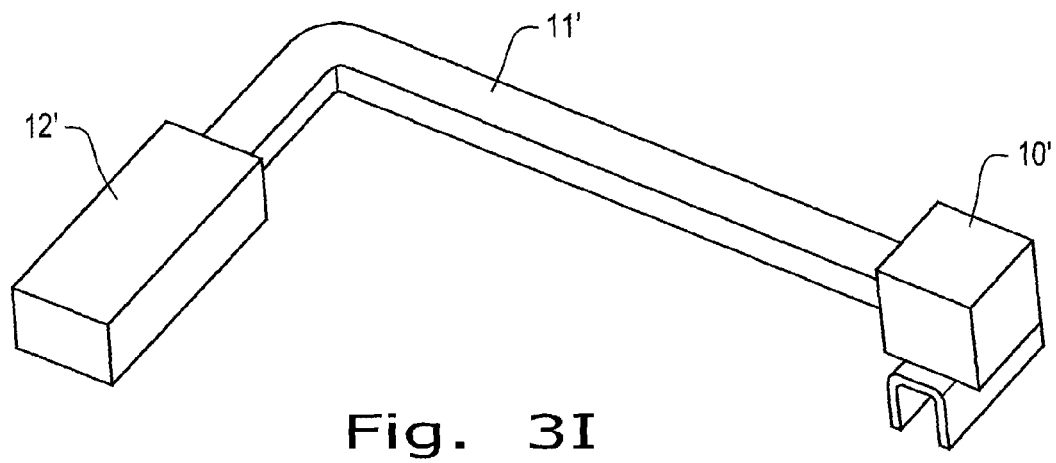
Figure 3J:
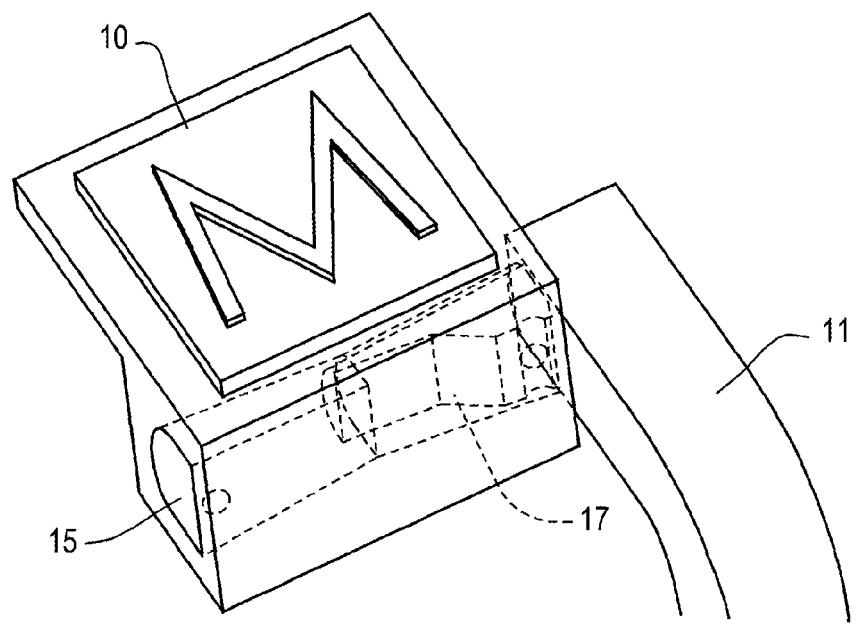

In one embodiment, the monitoring hardware includes a trackable pole that is attachable to the key and which has a particular identifying pattern. The attachment and the pole itself have known configurations so that observational data from the pole may be precisely mapped to the coordinate system and thus the progress of the surgical procedure may be monitored and recorded. For example, as particularly shown in FIG. 3J, key 10 may have hole 15 in a predetermined location specially adapted for engagement with insert 17 of pole 11. In such an arrangement, for example, poles 11 may be attached with a low force push into hole 15 of key 10, and an audible haptic notification may thus be given upon successful completion of the attachment.

It is further possible to reorient the pole during a surgical procedure. Such reorientation may be to change the location of the procedure, for example where a dental surgery deals with teeth on the opposite side of the mouth, where a surgeon switches hands, and/or where a second surgeon performs a portion of the procedure. For example, the movement of the pole may trigger a re-registration of the pole with relation to the coordinate system, so that the locations may be accordingly adjusted. Additionally, boundary conditions may be implemented in the software so that the user is notified when observational data approaches and/or enters the boundary areas.

In a further embodiment of the system utilizing the invention, a surgical instrument, termed a "hand piece" (not shown in FIGS. 3A-J, but see FIGS. 5 and 6 below), may also have a particular configuration that may be located and tracked in the coordinate system. A boundary condition may be set up to indicate a potential collision with virtual material, so that when the hand piece is sensed to approach the boundary condition an indication may appear on a screen, or an alarm sound. Further, target boundary conditions may be set up to indicate the desired surgical area, so that when the trajectory of the hand piece is trending outside the target area an indication may appear on screen or an alarm sound indicating that the hand piece is deviating from its desired path.

An alternative embodiment of some hardware components are shown in FIGS. 3O-1. Key 10' has connection elements with suitable connecting portions to allow pole 11' to position tracking marker 12' relative to the surgical site. Conceptually, key 10' serves as an anchor for pole 11' and tracking marker 12' in much the same way as the earlier embodiment, although it has a distinct shape. Software has the configuration of each particularly identified key and pole tracking marker, so that the location calculations are only changed according to the changed configuration parameters.

The materials of the hardware components may vary according to regulatory requirements and practical considerations. Generally, the key or fiducial component is made of generally radio opaque material such that it does not produce noise for the scan, yet creates recognizable contrast on the scanned image so that any pattern may be recognized. In addition, because it is generally being located on the patient, the material should be lightweight, suitable for connection to an apparatus on the patient (e.g. in the dental surgery example, connection to a plastic splint, in the surgical example, connected to the skin or particular tissue), and suitable for connection to a tracking pole.

For the material of the tracking pole, it should have sensing panels capable of tracking object sizes of about 1.5 cm squared, with relatively high contrast pattern engraving, optionally capable of resisting damage in autoclave process, with rigid, repeatable quick connection to a connector structure, with the ability to accommodate at least 4-6 different locations for different surgery locations, and like the key also be relatively lightweight as it will often be resting on or against the patient. Such a pole tracker may be made in an autoclave, with a connector in the form of shared amunst poles. While generally the pole tracker is connected by wire to a computing device to read the sensory input, the pole tracker may optionally have wireless connectivity to transmit the sensory data to a computing device.

In embodiments that additionally work with the optional hand piece of instrumentation, such a hand piece may also be lightweight and optionally capable of tracking objects the size of 1.5 cm squared; capable of operating in a 3 object array with 90 degrees relationship; optionally having a high contrast pattern engraving; and a rigid, quick mounting mechanism to a standard hand piece.

Figure 4A:
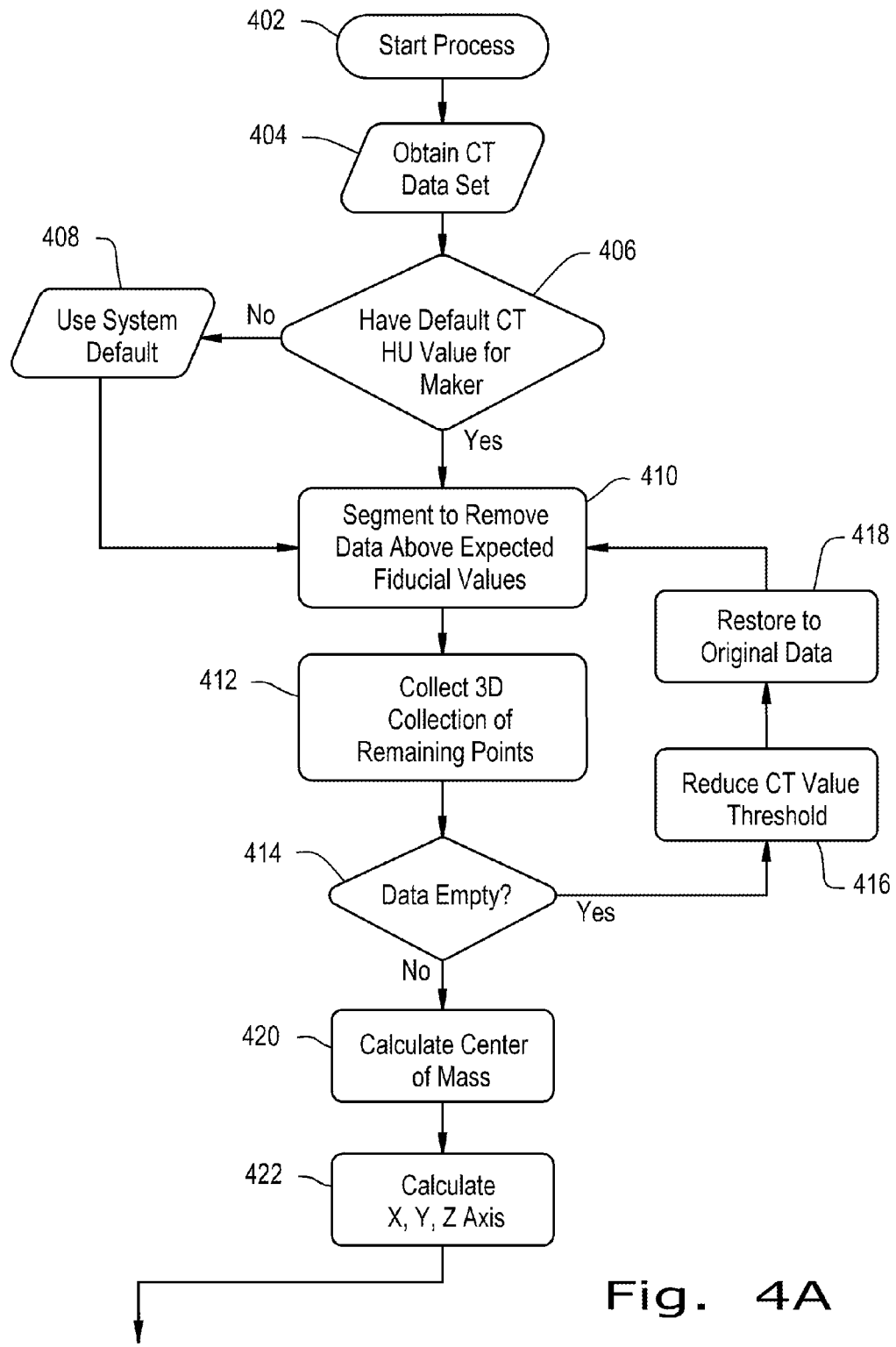
FIGS. 4A-C is a flow chart diagram illustrating one embodiment of the registering algorithm of the present invention.
Figure 4B:
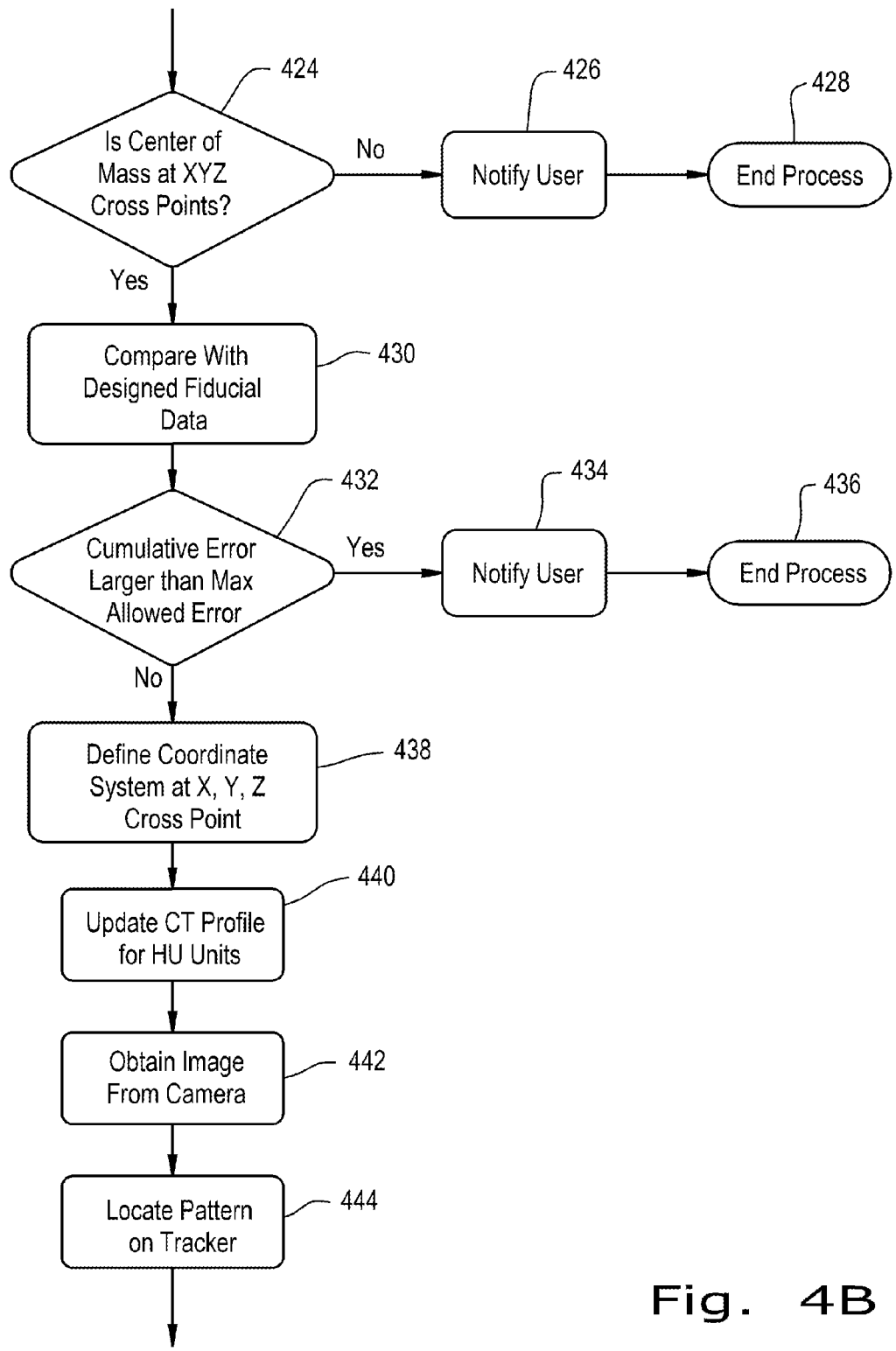
Figure 4C:
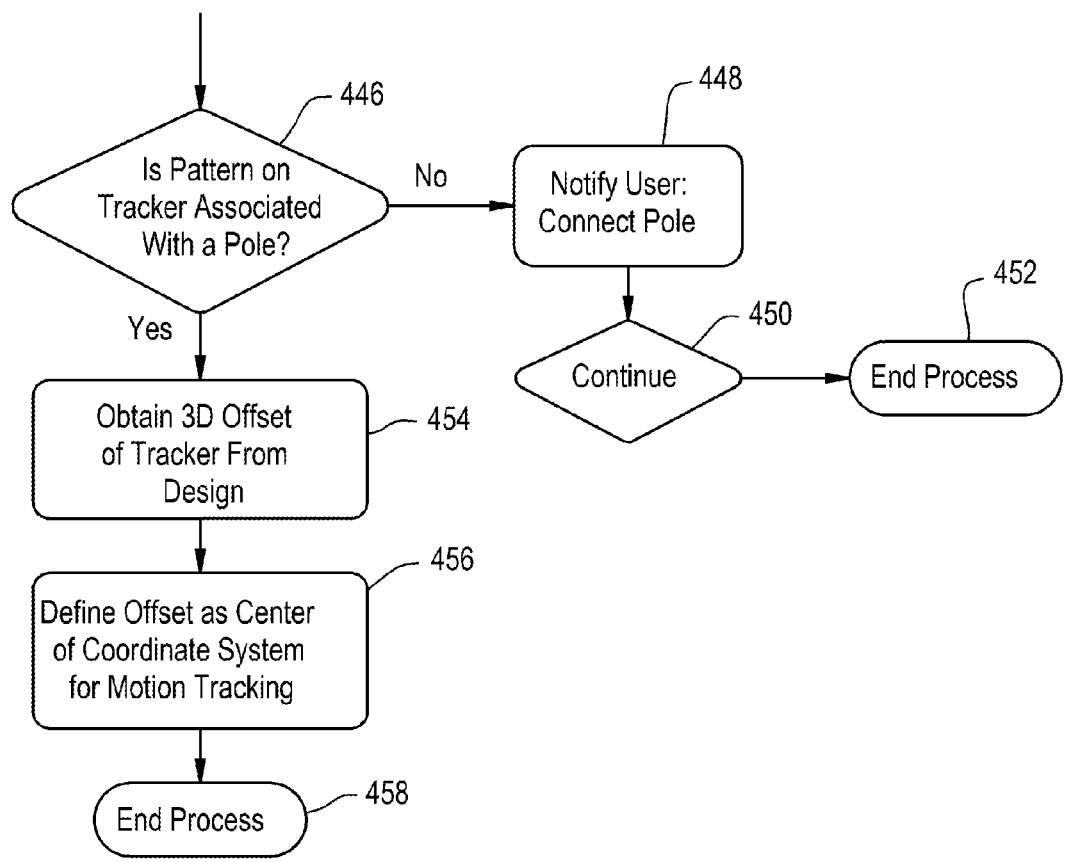

One embodiment of the invention utilizes an automatic registration method for tracking surgical activity, as illustrated in FIGS. 4A-C. Once the process starts at 402, the system obtains a data set (e.g. from a CT scanner) at 404 and checks for a Default CT Hounsfield unit (HU) value at 406, and if not present then the system default is used at 408. Next the data is processed by removing segments with data above the expected fiducial values at 410, followed by the collection of the remaining points at 412. If the data is empty at 414, the CT value threshold is reduced at 416, the original data restored at 418, and the segmenting process continues at 410. Otherwise, with the existing data a center of mass is calculated at 420 along with the X, Y, and Z axes at 422. If the center of mass is not at the XYZ cross point at 424, then the user is notified at 426 and the process stopped at 428. If the center of mass is at the XYZ cross point then the data points are compared with the designed fiducial data at 430. If the cumulative error at 432 is larger than the maximum allowed error then the user is notified at 434 and the process ends at 436. If not, then the coordinate system is defined at the XYZ cross point at 438, the CT profile is updated for the HU units at 440 and another image is obtained from a camera or other sensor at 442. Next, the pattern of the fiducial is located on the tracker at 444, and the pattern on the tracker is checked at 446 to see if associated with a pole. If not, then the user is notified to connect the pole at 448, continue without the pole connected at 450, and the processes ends at 452. If so, then the 3D offset of the tracker is obtained from the original design at 454 and that offset is defined as the center of the coordinate system for motion tracking at 456, and the registration process ends at 458. Other registration systems are also contemplated, for example using current other sensory data rather than the predetermined offset, or having a fiducial with a transmission capacity.

Figure 5:
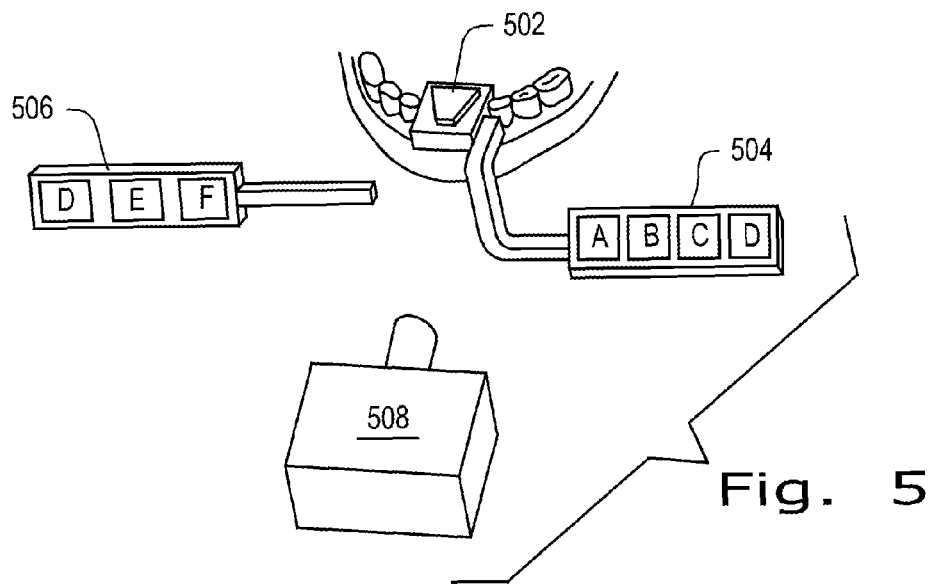
FIG. 5 is a drawing of a dental fiducial with a tracking pole and a dental drill according to one embodiment of the present invention.

One example of an embodiment of the invention is shown in FIG. 5. In addition to fiducial key 502 mounted at a predetermined tooth and having a tracker 504, an additional instrument 506, for example a dental drill, may be observed by camera 508

Figure 6:
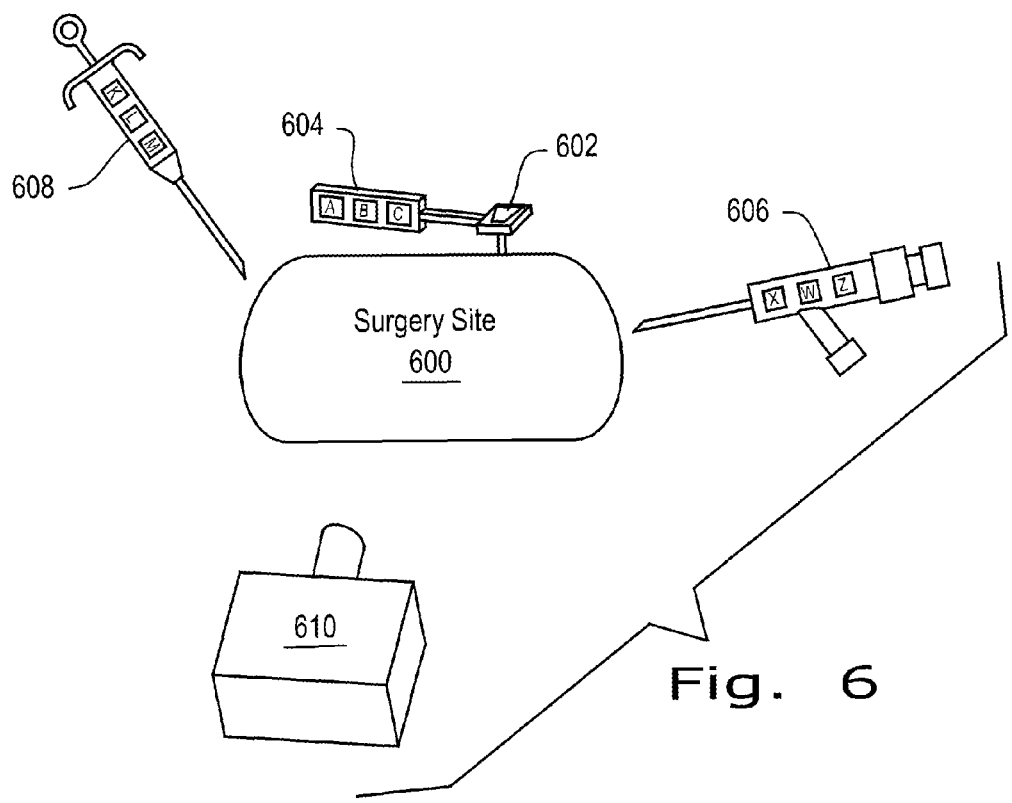
FIG. 6 is a drawing of an endoscopic surgical site showing the fiducial, endoscope, and biopsy needle according to another embodiment of the invention.

Another example of an embodiment of the invention is shown in FIG. 6. Surgery Site 600, for example a human stomach or chest, may have fiducial key 602 fixed to a predetermined position to support tracker arm 604. Endoscope 606 may have further markers, and biopsy needle 608 may also be present at Surgery Site 600. Sensor 610, for example a camera, infrared sensor, or radar.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method for monitoring a surgical site, comprising:
   attaching a key to a location proximate to a surgical site, the key having a marking perceptible on a scan;
   creating a first scan of the surgical location with the key attached;
   connecting a marker to the key;
   obtaining sensory data from a non-stereo sensor proximate the surgical site and communicating the sensory data to a computing device; and
   calculating and displaying a model of the surgical site by the computing device based on the scan, the identity of the key, and the observation data received from said tracker.

2. The method of claim 1 wherein the key consists of a specific material that is distinctly identifiable on an X-ray, Magnetic Resonance Imaging (MRI), computerized tomography (CT), sonography, or cone beam computerized tomography (CBCT).

3. The method of claim 1 wherein the connecting step includes using a plurality of markers attached to other items wherein said software program further determines the position and orientation of the plurality of markers.

4. The method of claim 1 wherein the key has a distinct shape which allows its position and orientation to be determined from the scan data.

5. The method of claim 1 wherein the key has a label in a predetermined position such that the orientation of the key is determined from scan data.

6. The method of claim 1 wherein the key is configured and arranged to fit the part of the patient being scanned.

7. The method of claim 1 wherein the marker has a distinct sensible characteristic which is identifiable in information from the sensor.

8. The method of claim 1 wherein the marker has a distinct shape such that the orientation of the key is determined from an image, or sequence of images, from the sensor.

9. The method of claim 1 wherein the marker is identifiable as a specific code determinable from sensor information.

10. The method of claim 1 wherein the marker is adaptable in its physical arrangement to permit unobstructed access to an operation site during different procedures or stages of a procedure.

11. The method of claim 1 wherein the step of connecting the marker involves using a mounting arrangement to connect the key and the marker, the mounting arrangement arranged such that the marker is removable such that a second marker is positionable in the mounting arrangement and the relative position of the second marker and the key is preserved.

12. The method of claim 9 wherein the specific code determines a specific marker whose position and orientation relative to the fiducial reference is known and fixed.

13. The method of claim 1 wherein the connecting step includes using a plurality of markers, each of the markers being attached to a corresponding implement such that the positions and orientations of the implements are determined by the computing device in the calculating step.

14. The method of claim 13 wherein the position and orientation of the plurality of markers is detected contemporaneously relative to the key.

15. The method of claim 13 wherein each of the plurality of markers are individually distinct so that identity of the attached implement is determinable from sensor information.

16. The method of claim 13 wherein each of the corresponding instruments has an operating point and the computing device determines the position of the operating point relative to the patient scan data.

17. The method of claim 16 wherein the operating point may be one of a drill bit of a dental drill, a sensor of an endoscope, and a blade of a scalpel.

18. The method of claim 13 wherein one of the corresponding instruments has multiple distinct identifiable markers attached to different parts of the one implement such at least one of the multiple distinct markers are apparent to the sensor in any orientation of the one implement.

19. The method of claim 13 wherein the implement is one of a dental drill, an endoscope, a biopsy needle and a surgical implant.

20. A method for monitoring a surgical site, comprising:
attaching a key to a location proximate to a surgical site, the key having a marking perceptible on a scan;
creating a first scan of the surgical location with the key attached;
connecting a marker to the key;
obtaining sensory data from a non-stereo sensor proximate the surgical site and communicating the sensory data to a computing device; and
calculating a transformational matrix to be used in displaying a visual representation of the surgical site by the computing device based on the scan, the identity of the key, and the observation data received from said tracker.

* * * * *